(12) United States Patent
Weber et al.

(10) Patent No.: US 10,238,855 B2
(45) Date of Patent: Mar. 26, 2019

(54) CONNECTOR WITH SEAL ELEMENT AND ADAPTED CONNECTOR PARTS

(71) Applicant: FRESENIUS MEDICAL CARE DEUTSCHLAND GMBH, Bad Homburg (DE)

(72) Inventors: Tobias Weber, St. Wendel (DE); Robert Berlich, St. Wendel (DE); Gerhard Mager, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 445 days.

(21) Appl. No.: 15/034,248

(22) PCT Filed: Nov. 4, 2014

(86) PCT No.: PCT/EP2014/002946
§ 371 (c)(1),
(2) Date: May 4, 2016

(87) PCT Pub. No.: WO2015/067359
PCT Pub. Date: May 14, 2015

(65) Prior Publication Data
US 2016/0287857 A1    Oct. 6, 2016

(30) Foreign Application Priority Data

Nov. 6, 2013   (DE) .................. 10 2013 018 639

(51) Int. Cl.
*F16L 37/248*    (2006.01)
*A61M 39/10*    (2006.01)
(Continued)

(52) U.S. Cl.
CPC .............. *A61M 39/10* (2013.01); *A61M 1/14* (2013.01); *A61M 39/1011* (2013.01);
(Continued)

(58) Field of Classification Search
CPC .......... A61M 39/1011; A61M 39/1055; A61M 2039/1033; A61M 2205/6081; A61M 39/20; F16L 37/248
See application file for complete search history.

(56) References Cited

U.S. PATENT DOCUMENTS 3,986,508 A    10/1976 Barrington
4,211,439 A    7/1980 Moldestad
(Continued)

FOREIGN PATENT DOCUMENTS

EP    1213472 A1 *  6/2002   ....... F02M 35/10144
EP    1331020 A1    7/2003
(Continued)

OTHER PUBLICATIONS

International Search Report for PCT/EP2014/002946 dated Feb. 5, 2015. 6 pages.
(Continued)

*Primary Examiner* — David Bochna
(74) *Attorney, Agent, or Firm* — Fish & Richardson P.C.

(57) ABSTRACT

Certain aspects of the invention relate to a connector including at least one first connector part and at least one second connector part. The connector parts can be connected to one another in a fluid-tight manner and can be locked to one another via at least one closure element. One of the connector parts has at least one sealing element (e.g., a septum or a sealing disk) that blocks a throughflow in the closed state and which can be opened, and the other one of the connector parts has at least one opening element for opening the sealing element. One of the connector parts has at least one projection and the other one of the connector parts has at least one receiver, and the opening element and the sealing element are arranged with respect to one another such that
(Continued)

the opening element only opens the sealing element when the projection has been introduced into the receiver.

22 Claims, 4 Drawing Sheets

(51) Int. Cl.
*F16L 37/38* (2006.01)
*A61M 1/14* (2006.01)
*A61M 39/20* (2006.01)
*A61M 39/00* (2006.01)

(52) U.S. Cl.
CPC ........ *A61M 39/1055* (2013.01); *A61M 39/20* (2013.01); *F16L 37/248* (2013.01); *F16L 37/38* (2013.01); *A61M 2039/009* (2013.01); *A61M 2039/1027* (2013.01); *A61M 2039/1033* (2013.01); *A61M 2039/1066* (2013.01); *A61M 2039/1072* (2013.01); *A61M 2205/276* (2013.01); *A61M 2205/6036* (2013.01); *A61M 2205/6081* (2013.01)

(56) References Cited

U.S. PATENT DOCUMENTS

| | | | |
|---|---|---|---|
| 4,511,359 A | 4/1985 | Vaillancourt | |
| 5,201,717 A | 4/1993 | Wyatt | |
| 5,292,308 A * | 3/1994 | Ryan | A61M 39/14 604/535 |
| 5,356,396 A * | 10/1994 | Wyatt | A61M 39/04 604/539 |
| 5,466,020 A | 11/1995 | Page | |
| 5,509,011 A | 4/1996 | Birth | |
| 5,509,911 A | 4/1996 | Cottone | |
| 5,658,260 A | 8/1997 | Desecki | |
| 6,402,207 B1 | 6/2002 | Segal et al. | |
| 6,612,624 B1 | 9/2003 | Segal et al. | |
| 8,070,189 B2 | 12/2011 | Yow et al. | |
| 8,257,287 B2 | 9/2012 | Hanlon et al. | |
| 8,287,517 B2 | 10/2012 | Hanlon et al. | |
| 8,377,039 B2 | 2/2013 | Utterberg et al. | |
| 8,613,731 B2 | 12/2013 | Hansen et al. | |
| 8,684,979 B2 | 4/2014 | Deighan et al. | |
| 2003/0144647 A1* | 7/2003 | Miyahara | A61M 39/162 604/523 |
| 2004/0111078 A1* | 6/2004 | Miyahara | A61M 39/162 604/414 |
| 2005/0150546 A1* | 7/2005 | Liepold | A61M 39/10 137/68.3 |
| 2007/0170719 A1* | 7/2007 | Lambert | F16L 37/248 285/148.14 |
| 2013/0079730 A1 | 3/2013 | Mosler et al. | |
| 2013/0270820 A1 | 10/2013 | Py | |

FOREIGN PATENT DOCUMENTS

| | | | |
|---|---|---|---|
| EP | 2937616 A1 * | 10/2015 | ............ A61M 39/10 |
| JP | 10-290842 | 11/1998 | |
| JP | 2008-73530 | 4/2008 | |
| JP | 2013-529520 | 7/2013 | |
| WO | WO9964103 A1 | 12/1999 | |
| WO | WO2006083333 A1 | 8/2006 | |
| WO | WO 2008/036935 | 3/2008 | |
| WO | WO2009024807 A1 | 2/2009 | |
| WO | WO 2012/000872 | 1/2012 | |
| WO | WO 2012/067584 | 5/2012 | |
| WO | WO 2013/158756 | 10/2013 | |
| WO | WO 2015/067359 | 5/2015 | |

OTHER PUBLICATIONS

International Preliminary Report on Patentability in International Application No. PCT/EP2014/002946, dated May 10, 2016, 10 pages.

* cited by examiner

CONNECTOR WITH SEAL ELEMENT AND ADAPTED CONNECTOR PARTS

CROSS-REFERENCE TO RELATED APPLICATIONS

This is the U.S. National Phase Application under 35 U.S.C. § 371 of International Patent Application No. PCT/EP2014/002946, filed Nov. 4, 2014, which claims the benefit of German Application No. 102013018639.0, filed Nov. 6, 2013, both of which are incorporated by reference herein. The International Application was published in German on May 14, 2015 as WO/2015/067359 2007/123138 A1 under PCT Article 21(3).

TECHNICAL FIELD

The present invention relates to a connector.

BACKGROUND

Treatment fluids are typically provided in bags in extracorporeal blood treatment. Depending on the type of therapy and on the patient needs, multiple different treatment fluids may be provided that differ in composition and in concentration of the individual solution components.

The bags generally have a connector part which can be connected to a complementary connector part. The complementary connector part can, for example, be attached to a fluid line. The bag connector part can be connected to the complementary connector part to remove the treatment fluid from the bag for the treatment and to transfer it, for example, into the fluid line to which the complementary connector part is attached.

In the event that multiple treatment fluids are used simultaneously in the therapy, there is a risk that the individual bags will be connected to the incorrect fluid line due to confusion of the user. This can result in an incorrect fluid being used for the blood treatment.

It is known from WO 09/024807 A1 to provide a connector including two connector parts with locking projections arranged on one connector part and complementary projections arranged on the other connector part that cooperate in the connected state and "emit" a connection signal. It is also known from WO 11/131783 A2 to connect a medication container to an injection apparatus via a connector having coded complementary connector parts.

SUMMARY

Certain aspects of the invention relate to a connector including at least one first connector part and at least one second connector part. The connector parts can be connected to one another in a fluid-tight manner and can be locked to one another via at least one closure element. One of the connector parts has at least one sealing element (e.g., a septum or a sealing disk) that blocks fluid flow therethrough in a closed state and which can be opened to permit fluid flow therethrough. The other one of the connector parts has at least one opening element for opening the sealing element. One of the connector parts has at least one projection and the other one of the connector parts has at least one receiver, and the opening element and the sealing element are arranged with respect to one another such that the opening element opens the sealing element when the projection has been introduced into the receiver.

Certain connectors described herein can reduce the likelihood of or prevent an incorrect treatment fluid from being supplied to a patient due to incorrect connector parts being connected to one another.

The two connector parts can be connected to one another in the manner of a bayonet connection.

The receiver and the projection can be located at peripheral regions of the connector parts.

In some cases, a connector part has an opening element, such as a cone, that cooperates with a septum or the like (e.g., a slit septum) in a specific position of the connector parts with respect to one another such that the opening element opens the septum. This is, however, only possible when the projection has been received in the receiver, which is in turn only the case when the two connector parts fit one another, i.e., are complementary, and which is not the case when the connector parts do not fit one another, i.e., are non-complementary. Opening of the septum does not occur with connector parts that are not complementary to one another since, in such a case, the projection cannot be introduced into the receiver to a sufficient degree to open the septum.

By preventing the septum from being opened when a user attempts to connect connector parts that are not complementary to one another, the administration of an incorrect fluid to the patient can be precluded.

The projection and the receiver, which serve as coding elements, thus are not only capable of holding the two connector parts to one another, e.g., in a shape-matching manner, and are not only coding elements, but also provide a solution for the need for security, according to which the administration of an incorrect treatment fluid can be reliably avoided when an incorrect connection is made, i.e., when a connection of non-complementary connector parts is made.

In certain aspects of the invention, the opening element of the one connector part can only break open or pierce the septum or the like (e.g., the slit septum) of the other connector part when the projection and the receiver of the connector parts are complementary, i.e., when the connector parts fit one another. If this is not the case, the opening element cannot generally break open or open the septum so that an incorrect infusion or administration of a treatment fluid can be reliably prevented.

The opening element can form a fluid channel of one of the connector parts.

Certain aspects of the invention relate to a connector including at least one first connector part and at least one second connector part. The connector parts can be connected to one another in a fluid-tight manner and can be locked to one another via at least one closure element. One of the connector parts has at least one sealing element with an aperture, e.g., a sealing ring, and the other one of the connector parts has at least one contact surface. One of the connector parts has at least one projection, and the other one of the connector parts has at least one receiver. The sealing element and the contact surface are arranged with respect to one another such that a fluid-tight connection is present between the first and the second connector parts when the projection has been introduced into the receiver.

If the connection of the two connector parts has not been correctly carried out, this is typically indicated by a leak because there is no fluid-tight connection between the two connector parts in this state. A fluid-tight connection in which no leak occurs to the outside is present when the connection has been correctly established, i.e., when the projection has been introduced into the receiver.

Instead of the sealing ring, any other suitable sealing element can also be used so that the term "sealing ring" does not only stand for a ring seal, but as a representative for peripheral sealing elements (e.g. a sealing cuff, a perforated disk, angular rings, etc.) having an aperture for receiving a connection stub.

Some aspects of the invention relate to a connector comprising at least one first connector part and at least one second connector part, wherein the connector parts can be connected to one another in a fluid-tight manner and can be locked to one another via at least one closure element. One of the connector parts has at least one projection and the other one of the connector parts has at least one receiver, and the projection can be introduced into the receiver with complementary connector parts.

The projection or the receiver can be part of an additional component, e.g., a ring-shaped or sleeve-shaped component, which is disposed over a section of the connector part and, in some cases, over its base body. The projection and/or the receiver can be parts of a separate component that is pushed over the base body.

This design can be economically advantageous since only one single base body type has to be manufactured. The single base body type can be combined with multiple different coding components and closure components.

While various features have been separately described above, it should be understood that those features can be provided in combination with one another in certain embodiments.

In some embodiments, the closure element is formed by at least one pin and by at least one groove-like receiver for this pin. In such embodiments, the groove can be configured such that it extends over a part region in an axial direction of the connector part and over a part region in the peripheral direction of the connector part so that a sliding movement and a rotary movement of the two connector parts relative to one another is necessary for the locking. In this case, the connection of the two connector parts thus takes place in a comparable manner to a bayonet connection.

One or more latch elements can be associated with the groove and can be contacted by the pin when the locking position of both contact parts is reached. These latch elements can both secure the locking and cause as they pass over of the pin. The noise can be perceived acoustically by the user to indicate to the user that the locking position has been reached. Alternatively or additionally, a haptic feedback can be generated when the contact parts reach the locking position, i.e., when the pin snaps over the latch element.

In certain embodiments, the pin is visible in the the locking position so that a visual indication of the locking position can be provided to the user.

In some embodiments, the additional part or another color marking, which is located on the connector part, is color-coordinated with the second connector part. The same can also apply accordingly to the second connector part. It is thus possible via a color design of the two connector parts or of additional elements, such as rings, etc., to indicate that the two connector parts are complementary, i.e., can be connected to one another.

In certain embodiments, the additional part or the other marking element are arranged such that they are also visible in the connected state of the connector parts so that a visual indication of the complementary connector parts is provided to the user.

In some embodiments, the additional part has a pressing surface, and the connector part on which the additional part is arranged has a sealing surface which is contacted by the sealing element (e.g., the ring seal or the septum). In such embodiments, the additional part not only bears the projection or the receiver, but also fixes the sealing element (e.g., the ring seal or of the septum) to the connector part.

The term "sealing element" used in the following is to be understood as overarching. It does not only stand for sealing disks in the manner of a septum, but also all other sealing elements that can be opened in sealing manner or that have an aperture for receiving a sealing surface of a stub.

In certain embodiments, the first connector part or the second connector part has a base body onto which the additional part is applied, and the base body has one or more latching noses which engage into at least one opening in the additional part. The connection between the latching noses and the opening can be configured such that it is not manually releasable. In such cases, it is possible to place the additional part onto a base body or onto a section of the base body and to lock it, e.g., by a latched connection, in a manner such that the additional part cannot be released, or can only be released with a considerable exertion of force from the base body after the latch connection has been established.

In some embodiments, the at least one projection is designed as an elevated portion which extends in the longitudinal direction and in the peripheral direction of a connector part and/or the receiver extends in the longitudinal direction and in the peripheral direction of the other connector part.

In certain embodiments, the projections and the receiver in complementary connector parts are dimensioned such that the at least one projection can be received into the receiver, and the projections and the receiver in parts which are not complementary are dimensioned such that the at least one projection cannot be received into the receiver. In some such embodiments, for example, the projections can be completely pushed into the receiver with complementary connector parts but not with non-complementary connector parts. This has the consequence that a pushing together of the connector parts is only possible, where it is possible at all, to the extent that the opening element does not open the septum, as has been described in more detail above, with non-complementary connector parts.

In some embodiments, the opening element is configured as a conically tapering stub which forms a region through which a fluid can flow when the connector parts are connected to one another. This stub can be set back with respect to the open end region of the connector part at which the connection with the other connector part is carried out to inhibit the stub from being contacted during mating of the connector parts.

In some embodiments, both connector parts have grip surfaces which lie in a common area in the locked state of the connector parts and which do not lie in a common area in the non-locked state of the connector parts. A visual indication of whether or not the two connector parts have been locked in the desired position is thus provided to the user. The connector parts can alternatively or additionally be configured to provide a haptic indication to the user when the connector parts reach a desired position relative to one another.

Embodiments can provide one or more of the following advantages.

In some embodiments, the connectors are designed such that no complete connection of the connector parts and thus no fluid flow through the connector is possible when incompatible connection parts are connected. The connectors can, for example, be designed so that the cone or stub of one of the connector parts stops in front of the sealing disk of the other connector part to prevent fluid communication between the connector parts.

In certain embodiments, color coding is used to indicate for the user which connector parts are compatible with one another.

The connectors described herein can provide intuitive handling. The principle of the bayonet connector, for example, is familiar to many users. Additionally, predefined grip surfaces of the connector parts can make the connectors easy to use.

In some embodiments, the connectors are designed such that no separate resilient element is required. It should be noted, however, that for embodiments using a sealing disk, a slight resilient effect may occur.

In certain embodiments, the connectors provide drip protection and fluid flow through the connector is prevented upon disconnecting the connector parts from one another. A sealing disk can, for example, be included in the connector to provide these functions.

In some embodiments, the connectors provide contact protection due to set-back sealing surfaces (as compared to standard Luer connections).

In certain embodiments, variable color coding is used to indicate for the user which of various different connector parts are compatible with one another.

In some embodiments, the connectors are configured such that only one component of the connector is in long-term contact with fluid flowing through the connector during use. That component can have the same design for multiple different connectors with different color and/or material variations, which can increase manufacturing efficiency.

In some embodiments, accidental disconnection of the connector parts is inhibited or prevented. In such embodiments, for example, the latch noses and the sealing element of the respective connector parts are configured to inhibit rotation of the connector parts relative to one another after connection. Security against disconnection can also be ensured on suddenly occurring tensile stresses due to the principle of the bayonet connection.

In some embodiments, in contrast to a screw movement, no engaging around is necessary on the closing of the connector.

In certain embodiments, the connector is configured such that the hose is only twisted by a few degrees upon connecting the connector parts to one another.

In some embodiments, there are a defined end position of the latched connection, defined latching forces, and a latched position with respect to the sealing elements in the interior of the connector.

In some embodiments, the connectors are configured to provide visual feedback of a closed connector by the aligned position of the grip surfaces and/or due to the visible bayonet connection.

In certain embodiments, the connectors are configured to provide acoustic feedback when the connector parts are locked relative to one another. The closure can, for example, be configured to latch audibly.

In some embodiments, the connectors are configured to provide haptic feedback when the connector parts are locked relative to one another. The closure can, for example, be configured to latch tangibly such that the user feels the feedback of such a locking movement.

In some embodiments, people with poor eyesight can also operate the connector "blind". It is not absolutely necessary to recognize the color coding of the connector for the correct connection.

In some embodiments, the base body and the universal protective cap (or an additional part) are the same for all connectors so that a cost reduction is possible with very high unit volumes.

Design of a universal protective cap or of a universal adapter is possible for all color and coding variations.

In some embodiments, the coding ring and the sealing element can be fixed at their respective positions without adhesive bonding or welding. These components can, for example, be non-releasable snap-in elements. Welding and adhesive bonding remains an optional possibility for the connection, however.

Other aspects, features, and advantages will be apparent from the following description.

DETAILED DESCRIPTION

Figure 1:
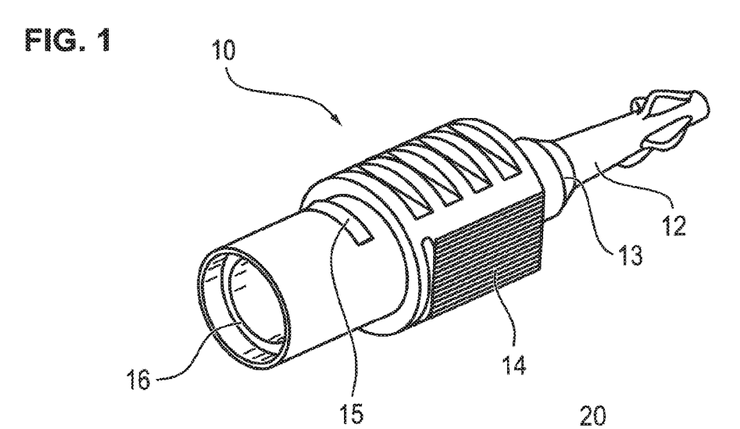
FIG. 1 is a perspective view of a base body of a first connector part.
Figure 2:
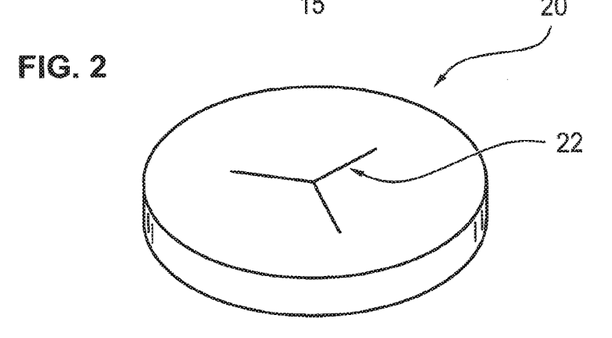
FIG. 2 is a perspective view of a septum of the first connector part.
Figure 3:
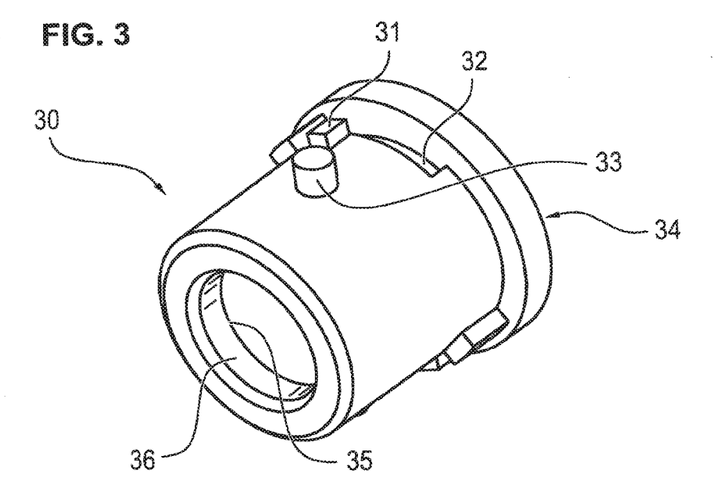
FIG. 3 is a perspective view of an additional component of the first connector part.

FIG. 1 shows a base body 10 that forms a first connector part together with a sealing element 20 shown in FIG. 2 and an additional part (a coding ring 30) shown in FIG. 3.

Figures 4, 5:
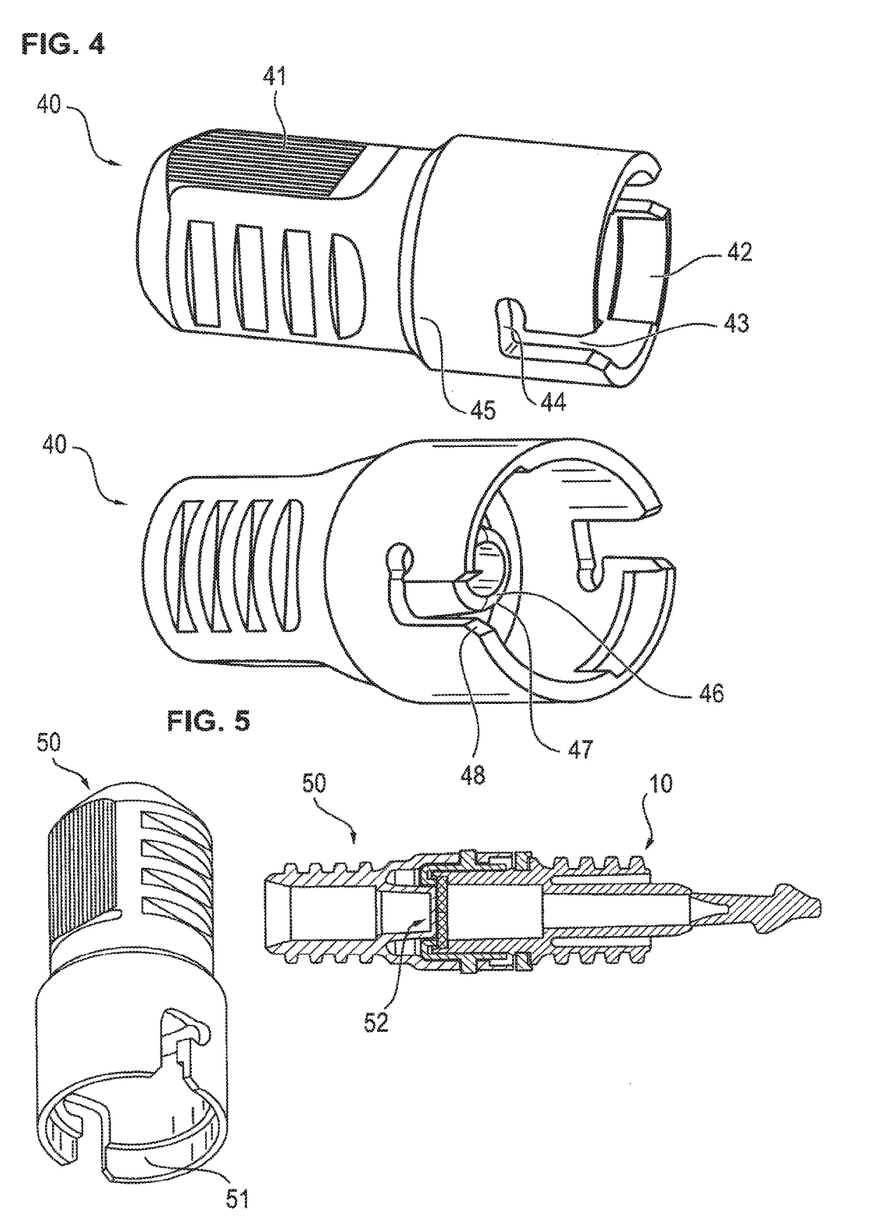
FIG. 4 shows different perspective views of a second connector part that can be connected to the first connector part.
FIG. 5 shows different views of a protective cap disconnected from the first connector part and connected to the first connector part.

A second connector part is formed by a hose connector 40 shown in FIG. 4.

The base body 10 shown in FIG. 1 can remain the same in all variants of the connector.

This brings about only one component (e.g., the base body 10) typically comes into contact with a medical solution or with a pharmaceutical during use.

Since color coding is carried out via the other connector components, namely via the coding ring 30 and the hose connector 40, any and all input by elutable or contact-active color granulates can be dispensed with in the base body 10 in accordance with FIG. 1. In this manner, interactions between any color granulates and medical solutions are reduced to a minimum since there are no material variations in direct contact with the medicaments or solutions.

In FIG. 1, reference numeral 12 shows a break-off cone, and reference numeral 13 shows a hose seat (solution side)

for plugging into a hose. These two parts form the solvent-contacting side of the connector part.

Reference numeral 14 designates a grip surface of the base body or of the first connector element which is flattened and which predefines the correct connection position intuitively by its haptics and optics.

A peripheral latch nose for connecting to the coding ring shown in FIG. 3 is shown by reference numeral 15. A weld connection is optionally also possible.

Reference numeral 16 designates a sealing surface for a sealing element shown by way of example in FIG. 2.

The sealing element in accordance with FIG. 2 having reference number 20 can, for example, be a sealing disk of silicone, for example, which has a slit opening 22. Optional sealing elements are an O ring, a sealing disk or also an element of different elasticity.

A different design of the sealing element can generally also be realized. A double seal can, for example, be realized by the introduction of a further sealing element.

Reference numeral 30 in FIG. 3 designates the coding ring which is configured to fit on the section of the base body shown at the left in FIG. 1.

The coding ring 30 is configured to provide a mechanical coding and a color coding with the hose connector 40 shown in FIG. 4. In addition, the coding ring 30 is configured to press and hold the sealing element 20. In some cases, the coding ring 30 can press and hold the sealing element 20 without the need for welding or adhesive bonding.

The geometry of the latch noses 15 of the base body 10 and of the openings 32 of the coding ring 30 can prevent rotation of the coding ring 30 relative to the base body 10. The coding ring 30 is, in some cases, non-releasably snapped onto the base body 10 or is welded or otherwise fixed there by the corresponding shape of the latch noses 15 of the base body 10.

In FIG. 3, reference numeral 31 shows coding pins, i.e., projections. The positions of the coding pins 31 can vary from connector to connector to help ensure that only complementary connector parts are used together.

These coding pins 31 extend, as can be seen in FIG. 3, in the longitudinal direction of the coding ring 30, on the one hand, and in the peripheral direction, on the other hand.

Reference numeral 32 designates the opening for the latch noses 15 of the base body 10. The opening 32 can serve as a security against rotation of the coding ring 30.

A pin for a bayonet connector is characterized by reference numeral 33. The pin 33 cooperates with a groove of the hose connector 40 in accordance with FIG. 4 and so forms the closure element.

A ring of the coding ring 30, also visible in the connected state, which serves as the color coding, is designated by reference numeral 34. The entire coding ring 30 can be colored.

The reference numeral 35 designates a pressing surface which is inwardly disposed and which is configured to press the sealing element 20, which in turn contacts the sealing surface 16 of the base body 10 in accordance with FIG. 1. The sealing element 20 is thus pressed between the base body 10 and the coding ring 30.

A recess which serves as a contact protection of the sealing element is designated by reference numeral 36.

The connection is for the most part unambiguous and non-confusable due to the coloring and due to the mechanical coding.

As stated above, FIG. 4 shows the hose connector 40 which forms the counter piece to the base body 10 and to the coding ring 30.

Only the respective correct hose connector 40 fits onto the correspondingly matching coding ring 30. The feedback of a performed and secure connection takes place both visually and acoustically as well as haptically.

As can be seen from FIG. 4, the coding ring 30 has flattened grip surfaces 41 which intuitively predefine the correct connection position. In the connected state, these grip surfaces 41 lie in one plane with the corresponding grip surfaces 14 of the base body 10.

Reference numeral 42 identifies a receiver that is configured as an inwardly disposed cut-out that extends peripherally about a portion of the connector part 40.

This cut-out 42 is configured to receive the coding pins 31 of the coding ring 30. Their position can vary from connector to connector.

An aperture or groove for the pin 33 of the bayonet connection of the coding ring 30 is designated by reference numeral 43. As can be seen from FIG. 4, a first portion of the groove 43 for receiving the pin 33 extends in the longitudinal direction of the hose connector, and a second portion of the groove 43 extends in the radial direction.

Latch elements, which are designated by reference numeral 44, are configured to secure the connection against self-release and to provide visual and haptic feedback. It can thus easily be detected by a user that a latching and thus a sufficient locking has taken place.

The color coding which delivers an unambiguous association between the hose connector 40 and the base body 10 or the coding ring 30 can, for example, take place via a completely colored hose connector 40 that has the same color as the coding ring 30 or via a colored ring attached (e.g., snapped on) to the hose connector 40. In either case, a color association between the hose connector and the first connector part, i.e., the base body or the coding ring 30 is achieved.

A cone (opening element) is designated by reference numeral 46. This cone 46 is configured to seal the connection with the aid of the elastic sealing element 20 of the first connector part.

A recess of the cone that provides a contact protection is identified by reference numeral 47, and a chamfer for easier fine positioning is identified by reference numeral 48.

Reference numeral 50 in FIG. 5 designates a protective cap that can be placed onto the base body 10 and that is provided with the coding ring 30. As can be seen from FIG. 5, this protective cap 50 has a peripheral coding cut-out 51 that extends about the entire periphery of the protective cap 50 so that the protective cap 50 can be placed onto any desired coding ring 30 and is thus universal. The use of a universal adapter could also be realized using this principle. Such a universal adapter could, for example, be used to provide a standard Luer connection on all connectors.

FIG. 5, right hand representation, is a sectional view of the first connector part connected to the protective cap 50. As illustrated, a support of the sealing disk in accordance with FIG. 2 takes place at the position 52 in order to hold the sealing disk closed, and thus leak tight, when not in use.

Figure 6:
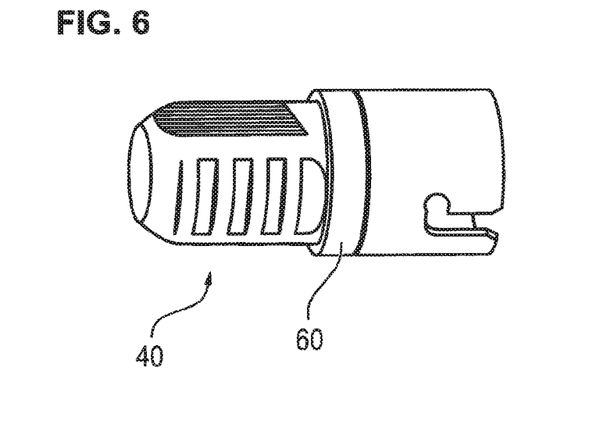
FIG. 6 is a perspective view of the second connector part with a color coding ring.

The hose connector 40 (the second connector part) is shown in FIG. 6. As can be seen from FIG. 6, a snapped-on color coding ring 60 has a different color than the hose connector itself. If a monochrome coding or a coloring of the hose connector itself should not be sufficient, the color range can be extended as desired by one or more such color coding rings 60. This naturally does not only apply to the side of the hose connector, but also to the side of the base body or of the coding ring.

It would also be possible by this color coding ring to dispense completely with colored plastics in the solution-contacting regions of the total connector.

Figure 7:
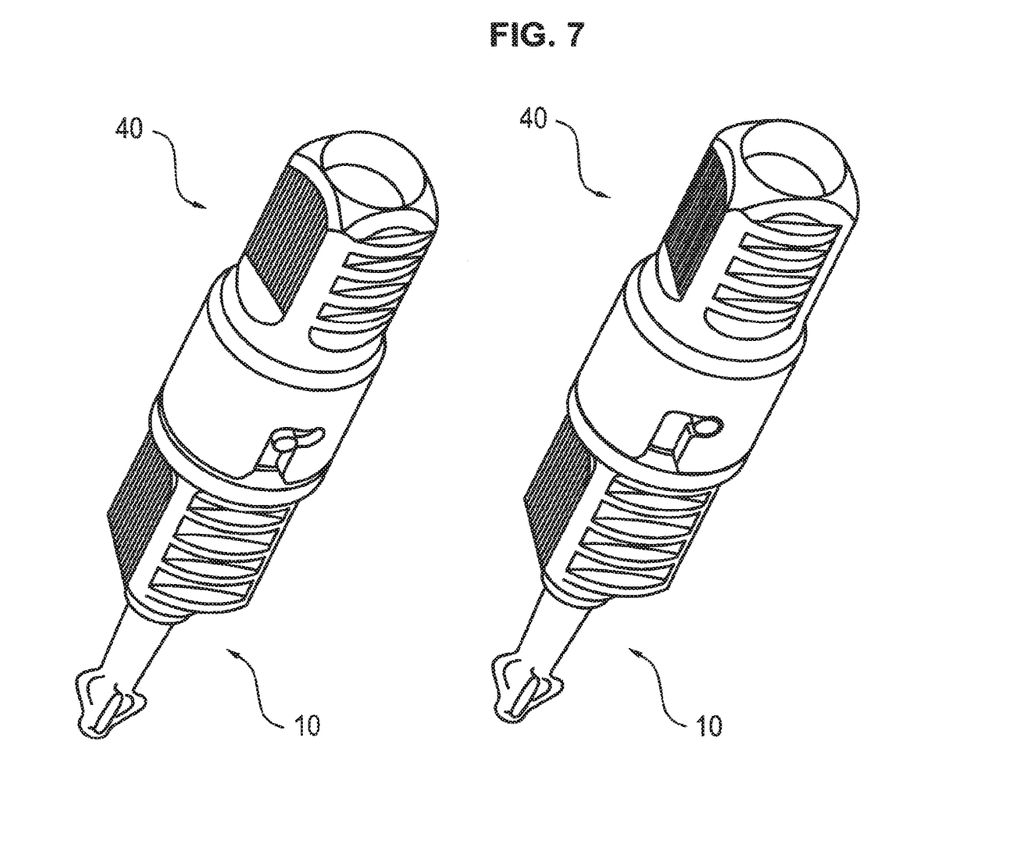
FIG. 7 shows different views of a connector including the first and second connector parts in a locked and an unlocked state.

The right hand and left hand representations of FIG. 7 illustrate the first and second connector parts with the latched connection open and closed, respectively.

As can be seen from FIG. 7, right hand representation, the grip region of the first connector part and the grip region of the second connector part are in one plane in the locked or closed position. The grip region of the connector is thus designed to be ergonomically grasped in the position in accordance with FIG. 7, left hand representation. The right hand representation in FIG. 7 is then reached by the rotary movement of the connector parts 10, 40 relative to one another.

Aligning the latch elements can be facilitated as a result of this configuration of the grip regions.

As can further be seen from FIG. 7, both the first and the second connector parts 10, 40 have curved regions whose radii with respect to the connector axis are larger than the spacing of the grip regions with respect to the connector axis. Both connector parts also have one or more almost flat or planar regions which form the grip region and which are set back with respect to the outer peripheries of the curved regions. The fluting in the grip regions also provides grip with a moist connector. Introduction slopes (e.g., chamfers) of the caps facilitate the fine positioning.

As can be seen from FIG. 7, right hand representation, the pin 33 of the coding ring 30 is received in the end region of the groove of the hose connector 40 in the locked position and is fixed there by the named latching elements. A visual indication of the complete locking is also possible in this manner.

Figure 8:
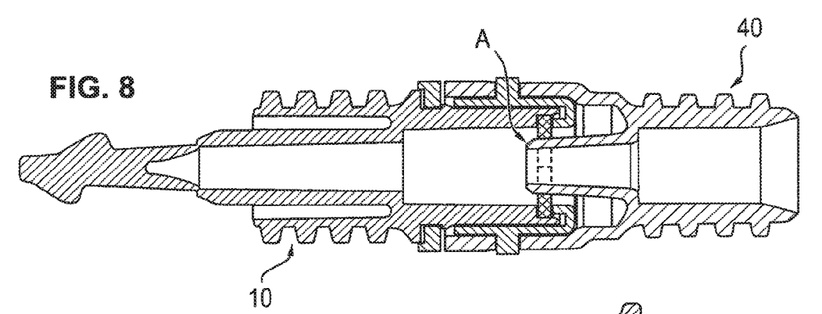
FIG. 8 is a sectional representation through the connector in the locked state.

FIG. 8 is a sectional representation of the first and second connector parts 10, 40 in a connected and locked state. As shown, the cone 46 penetrates the sealing disk 20 and opens the sealing disk 20 at the position A in the connected and locked state so that fluid flow through the connector is possible.

The connector is thus correctly connected.

Figure 9A:
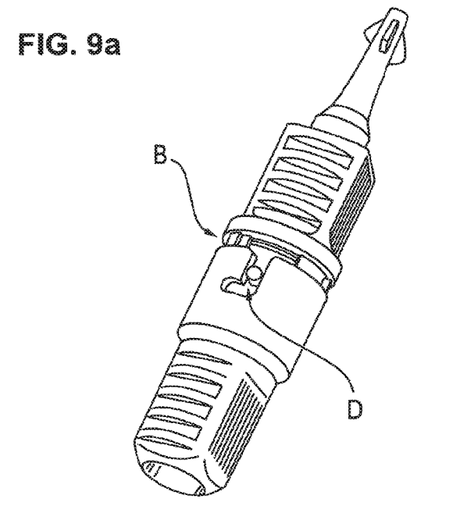
FIGS. 9a-9c are perspective representations of two connector parts that are not complementary.
Figure 9B:
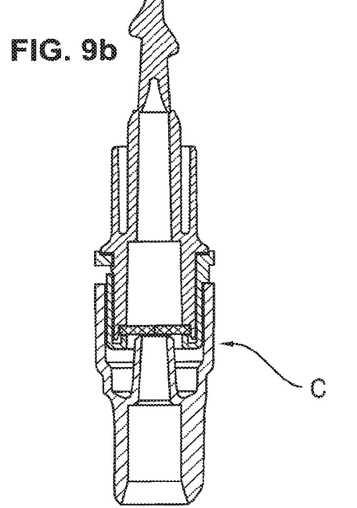
Figure 9C:
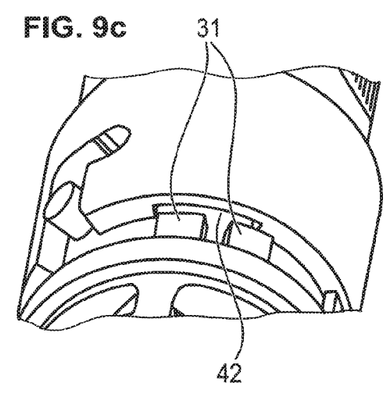

FIGS. 9a-9c show a situation in which two non-complementary connection parts, i.e., "wrong" connection parts, are partially connected to one another.

As can be seen from FIG. 9a, in this case, a gap is present at the point B and, due to the fact that the pin 33 is not yet received in the part of the groove extending in the peripheral direction, rotation of the first and second parts relative to one another is prevented.

As can be seen from FIG. 9b, the cone does not penetrate the sealing disk (refer to reference numeral C) so that no fluid flow through the connector is possible.

Complete connection of the connector parts is prevented due to the fact that, as shown in FIG. 9c, the coding pins 31 (projections) are wider than the receiver 42 of the coding ring such that the coding pins 31 cannot be introduced into the receiver 43.

Figure 10:
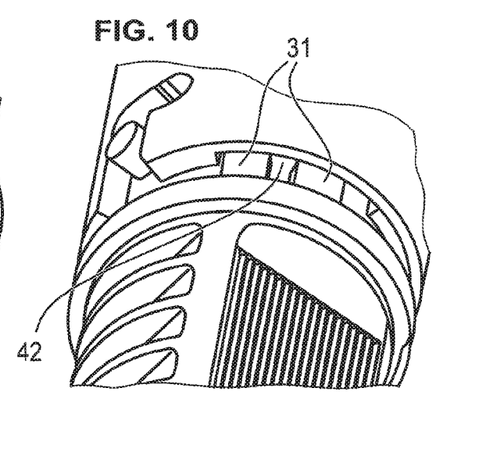
FIG. 10 is a representation of connector parts that are complementary to one another.

In contrast, FIG. 10 shows an embodiment with complementary connector parts in which the coding pins 31 fit into the cut-out 42 so that the gap B can be overcome and the two connector parts can be completely pushed together and then rotated to be locked.

The connectors described herein can provide a maximum mechanical security against confusion. No fluid flow through the connector is possible with incorrect connector parts since the cone or the opening element stops in front of the sealing disk or the septum.

A secure handling of connectors described herein is possible due to a color coding and due to the intuitive handling (generally of known bayonet connectors) with positioning aid by grip surfaces.

There is preferably no resilient element which engages directly at the pin as with a known bayonet connection. A resilience results by the septum which should not be understood as a resilient element in this sense.

On the disconnection, there is a drip protection and a throughflow barrier on a use of a sealing disk.

There is a contact protection due to the set-back sealing surfaces.

The color codings can be variable and can, for example, be formed by rings or other markings.

In some cases, the only component that is designed to contact the fluid flowing through the connector does not have color or material variations.

An accidental disconnection of certain connectors described herein can be prevented since the latching elements and the sealing element prevent a sole turning back. A maximum security against disconnection on suddenly occurring tensile stresses is ensured by the principle of the bayonet connection. In contrast to a screw movement, no engaging around is preferably necessary on the closing of the connector. A rotation by a few degrees is sufficient.

This is also advantageous with respect to the fact that the hose is accordingly only twisted only a little.

There are a defined end position of the latched connection, defined latching forces and a latched position with respect to the sealing elements in the interior of the connector.

The connection may not be made too light and also not too firm. It is typically made such that it is not self-releasing and also not too firm so that it is generally non-releasable.

The feedback of a closed connector can be fed back visually by the position of the grip surfaces and by the visible bayonet connector. An acoustic and haptic feedback is also possible and advantageous by a latching of the closure.

Persons with poor eyesight can also operate the connector largely "blind" since it is not absolutely necessary to use a color coding for the correct connection. These persons can, for example, orient themselves on the orientation of the grip surfaces or also on the acoustic or haptic feedback of the complete locking.

The base body in accordance with FIG. 1 and the universal protective cap in accordance with FIG. 5 can be the same for all connectors. A cost reduction is thus possible with very high unit volumes without compromises in security.

The same component can always be in contact with the solution during use.

The principle of the universal protective cap in accordance with FIG. 5 can also be reworked to a universal adapter which fits on all connectors.

The coding ring in accordance with FIG. 3 and the sealing element in accordance with FIG. 2 are typically fixed in their positions without adhesive bonding and welding, but only by non-releasable snap-in elements. Welding and adhesive bonding nevertheless remain an optional possibility of connection.

The number of possible permutations is theoretically unlimited due to the free number and positionability of the coding pins and is only restricted by the existing available space of the connector which is ultimately determined by the size of the connector.

By inserting e.g., a third coding pin, higher ranking solutions are possible which fit a plurality of subgroups, but not all subgroups. It is thus conceivable, for example, that a connector A and a connector B are admittedly incompatible between one another, but that a "main key C" fits both on the connector A and on the connector B. The "general key D" can then in turn fit on all counter pieces.

Some embodiments and aspects of the invention relate to a bayonet-like closing unit without a resilient element being necessary and relates to the mechanical coding of the connection by the coding pins.

The operation of the connector is self-explanatory, intuitive and secure against confusion and has a plurality of feedback options to the user whether the connection was closed correctly or not. Incorrect operations are also largely precluded with untrained technical personnel. The operability can also be carried out intuitively for laymen and for blind persons, also for patients who connect themselves, e.g., in home dialysis.

As stated above, the number of possible codings is only restricted by the size of the connector. It is possible to use a connector as a general key to implement a plurality of main keys having subgroups in this type of coding.

The area of use of dialysis was stated above. The connectors described herein, however, are not restricted to this area of use. A limitation to a medical indication is also not necessary. The connectors described herein can be used wherever a connection of a fluid line is desired in the low-pressure range with security against confusion and contact. It is not significant in this respect whether the principle is applied by a connector used once or used multiple times.

The invention claimed is:

1. A medical fluid line connector comprising:
   a base;
   a conduit portion having a peripheral sidewall extending axially from the base; and
   a shroud extending axially from the base, the shroud positioned circumferentially about the peripheral sidewall of the conduit portion, the shroud defining:
      a slot extending radially through a sidewall portion of the shroud, the slot having a first segment that extends axially from a distal end of the shroud toward a proximal end of the shroud, and a second segment that extends circumferentially from the first segment of the slot, and
      a recess that extends circumferentially along an inner surface of the sidewall portion of the shroud, the recess extending proximally from the distal end of the shroud, the recess being distal to the second segment of the slot,
   wherein the slot is configured to receive a radially extending bayonet pin of a complementary connector, the recess is configured to axially receive a radially extending projection of the complementary connector and to allow the projection to slide circumferentially within the recess, and the slot and the recess are arranged such that the bayonet pin slides axially into a proximal end of the first segment of the slot as the projection is axially received by the recess, and the bayonet pin slides circumferentially within the second segment of the slot as the projection slides circumferentially within the recess,
   wherein the slot and the recess are arranged such that a projection of a non-complementary connector is circumferentially offset from the recess when a bayonet pin of the non-complementary connector is disposed in the slot such that the projection cannot be received in the recess as the bayonet pin slides axially within the first segment of the slot, and
   wherein the conduit portion is configured to move axially through a septum of the complementary connector upon sliding the bayonet pin into the proximal end of the first segment of the slot and sliding the projection axially into the recess, and the conduit portion is configured to generate a fluid path between the base and the complementary connector upon movement of the conduit portion through the septum.

2. The medical fluid line connector according to claim 1, wherein the slot and the recess are arranged such that the projection of the non-complementary connector abuts a distal end of the sidewall portion adjacent the recess when the bayonet pin slides toward the distal end of the first segment of the slot.

3. The medical fluid line connector according to claim 1, wherein the slot and the recess are arranged such that the bayonet pin of the non-complementary connector cannot enter the second segment of the slot.

4. The medical fluid line connector according to claim 1, wherein the conduit portion is conical.

5. The medical fluid line connector according to claim 1, wherein the base is fluidly coupled to a medical fluid bag.

6. The medical fluid line connector according to claim 1, wherein the recess extends along an entire circumference of the sidewall portion.

7. The medical fluid line connector according to claim 1, wherein the base includes spaced apart gripping regions.

8. The medical fluid line connector according to claim 7, wherein the spaced apart gripping regions are positioned opposite one another.

9. The medical fluid line connector according to claim 8, wherein the spaced apart gripping regions are configured to be axially aligned with a second set of gripping regions on the complementary connector when the bayonet pin is moved to a terminal point in the second segment of the slot.

10. A medical fluid line connector comprising:
    a base having a cylindrical neck encircling a cylindrical space;
    a septum coupled to the cylindrical neck to seal the cylindrical space at a first end;
    a bayonet pin extending radially outward from the cylindrical neck; and
    a projection extending radially outward from the cylindrical neck, the projection being axially and circumferentially spaced from the bayonet pin,
    wherein the bayonet pin and the projection are arranged such that the bayonet pin slides axially into a proximal end of a first segment of a slot formed in a complementary connector as the projection is axially received by a recess of the complementary connector, and the bayonet pin slides circumferentially within a second segment of the slot as the projection slides circumferentially within the recess,
    wherein the bayonet pin and the projection are arranged such that the projection is circumferentially offset from a recess of a non-complementary connector when the bayonet pin is disposed in a first axially extending segment of a slot of the non-complementary connector such that the projection cannot be received in the recess of the non-complementary connector as the bayonet pin slides axially within the first axially extending segment of the slot, and
    wherein the septum is configured to axially receive a conduit extending from the complementary connector and thereby permit fluid communication between the cylindrical space of the fluid line connector and the conduit of the complementary connector when the bayonet pin slides axially into the proximal end of the first segment of the slot and the projection is axially received by the recess of the complementary connector.

11. The medical fluid line connector according to claim 10, wherein the bayonet pin and the projection are arranged such that the projection abuts a distal end of a sidewall portion adjacent the recess of the non-complementary connector when the bayonet pin slides toward an end of the first axially extending segment of the slot.

12. The medical fluid line connector according to claim 10, wherein the bayonet pin and the projection are arranged such that the bayonet pin cannot enter a second circumferentially extending segment of the slot of the non-complementary connector.

13. The medical fluid line connector according to claim 10, wherein the bayonet pin and the projection are positioned on a collar coupled to the cylindrical neck such that the collar is coaxial with the cylindrical neck.

14. The medical fluid line connector according to claim 13, wherein the collar is removably coupled to the cylindrical neck.

15. The medical fluid line connector according to claim 10, wherein the neck further comprises a tapered tab extending circumferentially along an outer wall of the cylindrical neck and the collar comprises a tapered slot extending circumferentially through the collar to receive the tapered tab.

16. The medical fluid line connector according to claim 10, wherein the base is fluidly coupled to a medical fluid bag.

17. A medical fluid line connector assembly comprising:
a first medical fluid line connector comprising
a first base having a cylindrical neck encircling a cylindrical space;
a septum coupled to the cylindrical neck to seal the cylindrical space at a first end;
a bayonet pin extending radially outward from the cylindrical neck; and
a projection extending radially outward from the cylindrical neck, the projection being axially and circumferentially spaced from the bayonet pin; and
a second medical fluid line connector configured to be releasably coupled to the first medical fluid line connector, the second medical fluid line connector comprising
a second base;
a conduit portion having a peripheral sidewall axially extending from the second base; and
a shroud extending axially from the second base, the shroud positioned circumferentially about the peripheral sidewall of the conduit portion, the shroud defining:
a slot configured to receive the bayonet pin, the slot extending radially through a sidewall portion of the shroud, the slot having a first segment that extends in an axial direction from a distal end of the shroud toward a proximal end of the shroud, and a second segment that extends circumferentially from the first segment of the slot, and
a recess configured to axially receive the projection and to allow the projection to slide circumferentially within the recess, the recess extending circumferentially along an inner surface of the sidewall portion of the shroud, the recess extending proximally from the distal end of the shroud, the recess being distal to the second segment of the slot,
wherein the slot and the recess are arranged such that the bayonet pin slides axially into a proximal end of the first segment of the slot as the projection is axially received by the recess, and the bayonet pin slides circumferentially within the second segment of the slot as the projection slides circumferentially within the recess,
wherein the slot and the recess are arranged such that a projection of a non-complementary connector is circumferentially offset from the recess when a bayonet pin of the non-complementary connector is disposed in the slot such that the projection cannot be received in the recess as the bayonet pin slides axially within the first segment of the slot, and
wherein the conduit portion of the second medical fluid line connector is configured to move axially through the septum of the first medical fluid line connector upon sliding the bayonet pin into the proximal end of the first segment of the slot and sliding the projection axially into the recess, and the conduit portion is configured to generate a fluid path between the first and second medical fluid line connectors upon movement of the conduit portion through the septum.

18. The medical fluid line connector according to claim 17, wherein the slot and the recess are arranged such that the projection of the non-complementary connector abuts a distal end of the sidewall portion adjacent the recess when the bayonet pin slides toward the distal end of the first segment of the slot.

19. The medical fluid line connector according to claim 17, wherein the slot and the recess are arranged such that the bayonet pin of the non-complementary connector cannot enter the second segment of the slot.

20. The medical fluid line connector according to claim 17, wherein at least one of the first base and the second base are fluidly coupled to a medical fluid bag.

21. A medical fluid line connector comprising:
a base;
a conduit portion having a peripheral sidewall extending axially from the base; and
a shroud extending axially from the base, the shroud positioned circumferentially about the peripheral sidewall of the conduit portion, the shroud defining:
a slot extending radially through a sidewall portion of the shroud, the slot having a first segment that extends axially from a distal end of the shroud toward a proximal end of the shroud, and a second segment that extends circumferentially from the first segment of the slot, and
a recess that extends circumferentially along an inner surface of the sidewall portion of the shroud, the recess extending proximally from the distal end of the shroud, the recess being distal to the second segment of the slot,
wherein the slot is configured to receive a radially extending bayonet pin of any of multiple different medical fluid line connectors, the recess is configured to axially receive a radially extending projection of any of the multiple different medical fluid line connectors and to allow the projection to slide circumferentially within the recess, and the slot and the recess are arranged such that the bayonet pin slides axially into a proximal end of the first segment of the slot as the projection is axially received by the recess, and the bayonet pin slides circumferentially within the second segment of the slot as the projection slides circumferentially within the recess, the projections of the multiple different medical fluid line connectors being located at different circumferential positions along those connectors, wherein the conduit portion is configured to move axially through a septum of one of the multiple different medical fluid line connectors upon sliding the bayonet pin of the one of the multiple different medical fluid line connectors into the proximal end of the first segment of the slot and sliding the projection of the one of the multiple different medical fluid line connectors axially into the recess, and the conduit portion is configured to generate a fluid path between the base and the of the one of the multiple different medical fluid line connectors upon movement of the conduit portion through the septum.

22. A method comprising:

connecting a first medical fluid line connector, configured for coupling to each of multiple different second medical fluid line connectors, to one of the second medical fluid line connectors, the first medical fluid line connector comprising a shroud defining:
- a slot extending radially through a sidewall portion of the shroud, the slot having a first segment that extends axially from a distal end of the shroud toward a proximal end of the shroud, and a second segment that extends circumferentially from the first segment of the slot, and
- a recess that extends circumferentially along an inner surface of the sidewall portion of the shroud, the recess extending proximally from the distal end of the shroud, the recess being distal to the second segment of the slot, wherein the slot is configured to receive a radially extending bayonet pin of any one of the multiple different second medical fluid line connectors, the recess is configured to axially receive a radially extending projection of any one of the multiple different second medical fluid line connectors and to allow the projection to slide circumferentially within the recess, and the slot and the recess are arranged such that the bayonet pin slides axially into a proximal end of the first segment of the slot as the projection is axially received by the recess, and the bayonet pin slides circumferentially within the second segment of the slot as the projection slides circumferentially within the recess, wherein the projections of the multiple different second medical fluid line connectors are located at different circumferential positions along those connectors, and connecting the first medical fluid line connector to one of the multiple different second medical fluid line connectors comprises sliding the bayonet pin of the one of the multiple different second medical fluid line connectors into the slot of the first medical fluid line connector and rotating the first medical fluid line connector with respect to the one of the multiple different second medical fluid line connectors such that the projection slides circumferentially within the recess.

* * * * *

UNITED STATES PATENT AND TRADEMARK OFFICE
CERTIFICATE OF CORRECTION

PATENT NO. : 10,238,855 B2
APPLICATION NO. : 15/034248
DATED : March 26, 2019
INVENTOR(S) : Tobias Weber, Robert Berlich and Gerhard Mager Page 1 of 1

It is certified that error appears in the above-identified patent and that said Letters Patent is hereby corrected as shown below:

In the Claims

Claim 21
Column 15, Line 14, delete "the of the" and insert --the--.

Signed and Sealed this
Twenty-first Day of May, 2019

Andrei Iancu
*Director of the United States Patent and Trademark Office*